United States Patent [19]
Johnson et al.

[11] Patent Number: 5,304,571
[45] Date of Patent: Apr. 19, 1994

[54] UNBUFFERED PREMIXED RANITIDINE FORMULATION

[75] Inventors: Douglas G. Johnson, Grayslake; Allan E. Titus, Round Lake, both of Ill.

[73] Assignee: Baxter International Inc., Deerfield, Ill.

[21] Appl. No.: 910,467

[22] Filed: Jul. 8, 1992

Related U.S. Application Data

[62] Division of Ser. No. 793,043, Nov. 15, 1991, Pat. No. 5,169,864.

[51] Int. Cl.$^5$ .......................... A61K 31/34; A61L 2/00
[52] U.S. Cl. ..................... 514/471; 53/425; 206/524.1
[58] Field of Search .......... 514/471; 53/425; 206/524.1

[56] References Cited

U.S. PATENT DOCUMENTS

| | | |
|---|---|---|
| 3,950,333 | 4/1976 | Durant et al. |
| 4,001,323 | 1/1977 | Felder et al. |
| 4,021,481 | 5/1977 | Almen et al. |
| 4,024,271 | 5/1977 | Durant et al. |
| 4,128,658 | 12/1978 | Price et al. |
| 4,250,113 | 2/1981 | Nordal et al. |
| 4,255,440 | 3/1981 | Price et al. |
| 4,279,819 | 7/1981 | Price et al. |
| 4,396,597 | 8/1983 | Rakli et al. |
| 4,521,431 | 6/1985 | Crookes. |
| 4,585,790 | 4/1986 | Padfield et al. ............ 514/471 |
| 4,955,871 | 9/1990 | Thomas ............ 604/217 |
| 5,042,975 | 8/1991 | Chien et al. ............ 604/20 |
| 5,068,249 | 11/1991 | Long ............ 514/471 |
| 5,169,864 | 12/1992 | Johnson et al. ............ 514/471 |

OTHER PUBLICATIONS

Das Gupta et al C.A. 110: 44828v (1989) of J. Clin. Pharm. Ther 13(5): 329–334 (1988).
Lampsona et al C.A. 105: 11922q (1986) of Am. J. Hosp. Pharm. 43(4): 921–5 (1986).
Bullock C.A. 111: 239397q (1989) of DICP Ann. Pharmacother. 23(10) 544–546 (1989).
Sarkar et al C.A. 115: 263242f (1991) of Am. J. Hosp. Pharm. 48(10): 2184–6 (1991).
Galante et al C.A. 113: 217962b (1990) of Am. J. Hosp. Pharm. 47(7): 1580–4 (1990).
Karnes et al C.A. 110: 179377t (1989) of Am. J. Hosp. Pharm. 46(2): 304–7 (1989).
Avis "Sterile Products" in Lachman et al, The Theory and Practice of Industrial Pharmacy (2nd. Ed) (1976) pp. 586 to 591, 598 to 600.
Galante et al, Stability of Ranitidine Hydrochloride at Dilute Concentration in Intravenous Infusion Fluids at Room Temperature, American Journal of Hospital Pharmacy, vol. 47, Jul. 1990, pp. 1580–1583.
Lampasona et al, Stability of Ranitidine Admixtures Frozen and Refrigerated in Minibags, Am. Journal of Hospital Pharmacy, vol. 43, Apr. 1986, pp. 921–924.

*Primary Examiner*—Shep K. Rose
*Attorney, Agent, or Firm*—Paul E. Schaafsma; Amy L. H. Rockwell; Paul C. Flattery

[57] ABSTRACT

A pharmaceutical composition is provided comprising an unbuffered iso-osmotic aqueous formulation containing an effective amount of ranitidine for the treatment of conditions mediated through histamine $H_2$ receptors. The formulation has a pH of greater than or equal to 5.0 and less than 6.5 and preferably includes an osmotic adjusting agent chosen from the group consisting of dextrose and sodium chloride.

4 Claims, 3 Drawing Sheets

UNBUFFERED PREMIXED RANITIDINE FORMULATION

This is a division of application Ser. No. 07/793,043, filed on Nov. 15, 1991 now U.S. Pat. No. 5,169,864.

BACKGROUND OF THE INVENTION

The present invention relates generally to pharmaceutical compositions. More specifically, the present invention relates to premixed ranitidine formulations.

Ranitidine [N-[2-[[[5-(dimethylamino) methyl-2-furanyl]methyl]thio]ethyl]-N'-methyl-2-nitro-1,1-ethenediamine] is a histamine $H_2$ antagonist that blocks the secretion of gastric acid and is widely used to treat peptic ulcer disease. Oral and parenteral formulations including ranitidine are known.

Typically, pharmaceutical products must be discarded after they degrade to less than 90% potency. One of the problems encountered with ranitidine formulations is that they suffer the disadvantage of degradation during terminal sterilization. This can be compensated for by manufacturing overages, but doing so means that when the product is at 100% potency, it already contains several % degradation.

U.S. Pat. No. 4,585,790 ('790 patent) discloses an aqueous based ranitidine formulation that is buffered so that it has a pH in the range of 6.5 to 7.5. Citrate and phosphate salts are used as buffers. The '790 patent states that a buffered ranitidine formulation is particularly stable when compared with a ranitidine formulation having a lower pH. Indeed, the patent states that "... the rate of breakdown in ranitidine is about 10 times faster for a solution buffered to a pH of 5.5 than for a solution buffered to pH 7.0."

Examples of buffered admixed ranitidine formulations and short term stability testing of same are discussed in: Galante et al, *Stability of Ranitidine Hydrochloride at Dilute Concentration in Intravenous Infusion Fluids at Room Temperature*, American Journal of Hospital Pharmacy, Vol. 47, July 1990, pp. 1580–1583; and Lampasona et al, *Stability of Ranitidine Admixtures Frozen and Refrigerated in Minibags*, American Journal of Hospital Pharmacy, Vol. 43, April 1986, pp. 921–925.

Of course, the addition of a buffer to a formulation increases the cost and time necessary to prepare the formulation. A further disadvantage with respect to a formulation such as that disclosed in the '790 patent, is that during sterilization of the formulation, approximately 4 to 8% of the ranitidine degrades.

SUMMARY OF THE INVENTION

The present invention provides an improved premixed pharmaceutical composition including ranitidine. In an embodiment of the present invention, a pharmaceutical composition comprising a sterile premixed unbuffered aqueous formulation containing an effective amount of ranitidine for the treatment of conditions mediated through histamine $H_2$ receptors is provided. Preferably, the pH of the composition is less than 6.5.

In an embodiment, a pharmaceutical composition comprising a sterile premixed aqueous formulation containing an effective amount of ranitidine for the treatment of conditions mediated through histamine $H_2$ receptors is provided, the formulation having a pH in the range of less than 6.5 to about 5.0.

In an embodiment, the formulation includes an osmotic adjusting agent chosen from the group consisting of mannitol, glycerol, dextrose, and sodium chloride.

In an embodiment, the composition is terminally sterilized.

In an embodiment, the composition is sterile filled into a container.

In an embodiment, the concentration of ranitidine in the product is approximately 0.1 mg/ml to about 1.3 mg/ml.

The present invention also provides a process for making a premixed pharmaceutical composition including ranitidine, that in an embodiment, comprises the steps of: dissolving ranitidine in a diluent and maintaining the pH of the resultant formulation at a pH of between less than 6.5 and greater than or equal to 5.0; sterilizing the formulation by passing it through a filter into a container; and sealing the container.

In another embodiment, a process for making a premixed pharmaceutical composition including ranitidine is provided comprising the steps of: dissolving ranitidine in a diluent and maintaining the pH of the resultant formulation at a pH of between less than 6.5 and greater than or equal to 5.0; and placing the formulation in a container and sterilizing same by steam sterilization.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
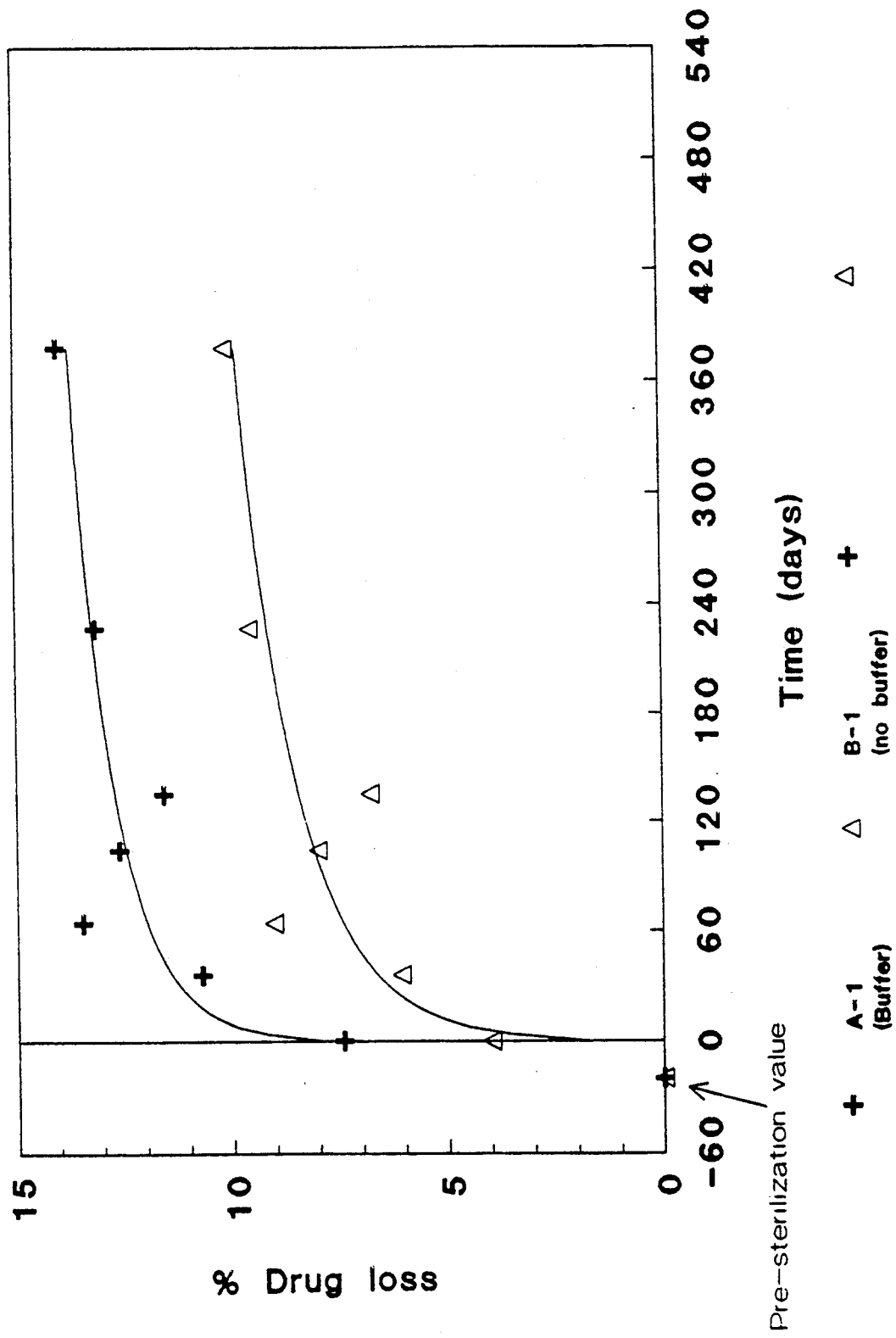
FIG. 1 illustrates graphically a comparison of drug degradation over time for a buffered ranitidine formulation and a ranitidine formulation prepared pursuant to the present invention.

The present invention provides an improved ranitidine formulation. The inventors have found that pursuant to the present invention a premixed formulation can be provided that does not require buffering but, however, provides stability for long term storage. Furthermore, the present invention provides a formulation wherein the drug loss during sterilization of the formulation is reduced as compared to a buffered solution.

To this end, a premixed unbuffered iso-osmotic formulation of ranitidine is provided. Preferably, the formulation has a pH range from approximately 5.0 to less than 6.5. The formulation provides long term storage that is substantially similar to formulations with a buffer. However, additionally, the formulation is more stable, than a buffered formulation, with respect to the stresses of terminal sterilization.

It has been found that a formulation having a pH range of 5.0 to less than 6.5 provides many other advantages with respect to buffered formulations. In this pH range, hydrolysis of ranitidine is minimized. By eliminating the requirement of a buffer, processing steps required to add the buffer are also eliminated. This reduces the cost of the formulation. Likewise, the number of components that must be considered when administering the formulation to a patient, are reduced. This also reduces the cost of the formulation.

Because the formulation is iso-osmotic, the formulation is more conducive to intravenous infusion. In this regard, the composition will not cause problems associated with localized changes in osmotic pressures.

The formulation includes a diluent, osmotic adjusting agent. Preferably, the agent is either dextrose or sodium chloride. However, other osmotic adjusting agents can be utilized, such as mannitol or glycerol.

Although the preferred embodiments of the formulation set forth herein are for parenteral compositions, the aqueous formulations of the present invention can be constructed so that they can be administered enterally. In this regard, if desired, conventional excipients can be added, such as sweeteners, flavoring aids, viscosity enhancing agents, and preservatives. For example: viscosity enhancing agents can include sorbitol, cellulose derivatives, glycerol, and Xanthan gum; preservatives can include alkyl hydroxyl benzoates; and sweeteners can include sorbitol, sucrose, and saccharins.

In an embodiment, the present invention provides a sterile premixed parenteral formulation comprising ranitidine and sodium chloride. A formulation that has been found to function satisfactorily is 1 mg/ml ranitidine and 9 mg/ml sodium chloride in sterile water.

The pH of the formulation can be adjusted using an appropriate adjuster such as hydrochloric acid or sodium hydroxide. As stated above, the pH of the formulation is less than 6.5 and greater than or equal to 5.0. The concentration of the ranitidine in the formulation can be from 0.2 mg/ml to 1.3 mg/ml ranitidine.

The formulation is terminally sterilized, through steam sterilization, after being packaged. Perferably, the formulation is packaged in flexible plastic containers; if desired, however, the formulation can be packaged in glass. It is believed that the formulation will have a shelf life of at least twelve months.

In an embodiment, another sterile premixed parenteral formulation is provided comprising ranitidine and dextrose. A formulation that has been found to function satisfactorily comprises 1 mg/ml ranitidine and 5% (weight/volume) dextrose in water. The pH is adjusted using hydrochloric acid.

Individual units of the formulation can be made by passing the solution through a 0.22µ filter and filling the units. In this regard, the composition can be sterile filled into a container to avoid the heat stress of terminal sterilization.

The formulation of the present invention provides an unbuffered composition that has a stability (shelf life) within 2% of a buffered composition such as that which is disclosed in U.S. Pat. No. 4,585,790. Additionally, however, the composition remains stable during terminal sterilization in contrast to the composition disclosed in the '790 patent which degrades 4 to 8% during terminal sterilization.

By way of example, and not limitation, examples of the present invention will now be given.

EXAMPLE 1

In this example, the stability during long term storage of a buffered ranitidine solution and an unbuffered ranitidine solution having a pH of 6.3, prepared pursuant to the present invention, were examined. The pHs were measured using a calibrated digital pH meter and combination electrode. The formulations tested were as follows:

| Test Configurations: | A-1 | B-1 |
| --- | --- | --- |
| Bag Material | PVC | PVC |
| Plastic Bag Size | 50 ml | 50 ml |
| Concentration (mg/ml) | 0.5 | 0.5 |
| Buffer | phos/cit | none |
| Diluent | .45% NaCl | .45% NaCl |
| pH (initial) | 7.0 | 6.5 |

The formulations in the plastic containers were terminally sterilized through steam sterilization. The formulations were then placed in temperature controlled storage conditions. Ranitidine degradation was measured using high-performance liquid chromatography (HPLC) with a stability-indicating assay that has been validated and shown to be reproducible and accurate.

| Results: | | |
| --- | --- | --- |
| pH after sterilization | 7.0 | 6.1 |
| % loss on sterilization | 7.4% | 4% |
| Additional loss over 36 days @ 55° | 13% | 11% |
| Additional loss over 104 days @ 25° | 5.2% | 4% |
| Additional loss over 378 days @ 25° | 6.6% | 6.1% |
| pH after 378 days @ 25° C. | 7.0 | 5.8 |

Comments

FIG. 1 illustrates graphically the results of the experiment at a storage of 25° C.

The loss over sterilization was found to be less for the non-buffered ranitidine solution than for the buffered ranitidine solution. It is interesting to note that the non-buffered solution is at a pH that was believed to be less stable than the pH for the buffered solution.

Storage at 25° C. did not seem to induce significant additional drug loss. Units of both formulations were filled with headspaces of 0 and 20 ml air. No significant difference was determined in the degradation of the units using the two headspaces.

EXAMPLE 2

In this example, a buffered ranitidine formulation was compared to a non-buffered formulation having a pH of 5.5. The formulations tested were as follows:

| Test Configurations: | A-2 | B-2 |
| --- | --- | --- |
| Bag Material | Minimally Plasticized PVC | Minimally Plasticized PVC |
| Bag Size | 250 ml | 250 ml |
| Concentration (mg/ml) | 0.5 | 0.5 |
| Buffer | phos/cit | none |
| Diluent | .45% NaCl | .45% NaCl |
| pH (initial) | 7.0 | 5.6 |

Again, the products were terminally sterilized (steam sterilization) and stored. Ranitidine degradation was measured as in Example 1.

| Results: | | |
| --- | --- | --- |
| pH after sterilization | 7.0 | 5.9 |
| % loss on sterilization | 5% | 3% |

-continued

| Results: | | |
|---|---|---|
| Loss over 35 days @ 55° | 4.6% | 5.3% |
| Loss over 103 days @ 25° | 0 | 0 |

Comments

Figure 2:
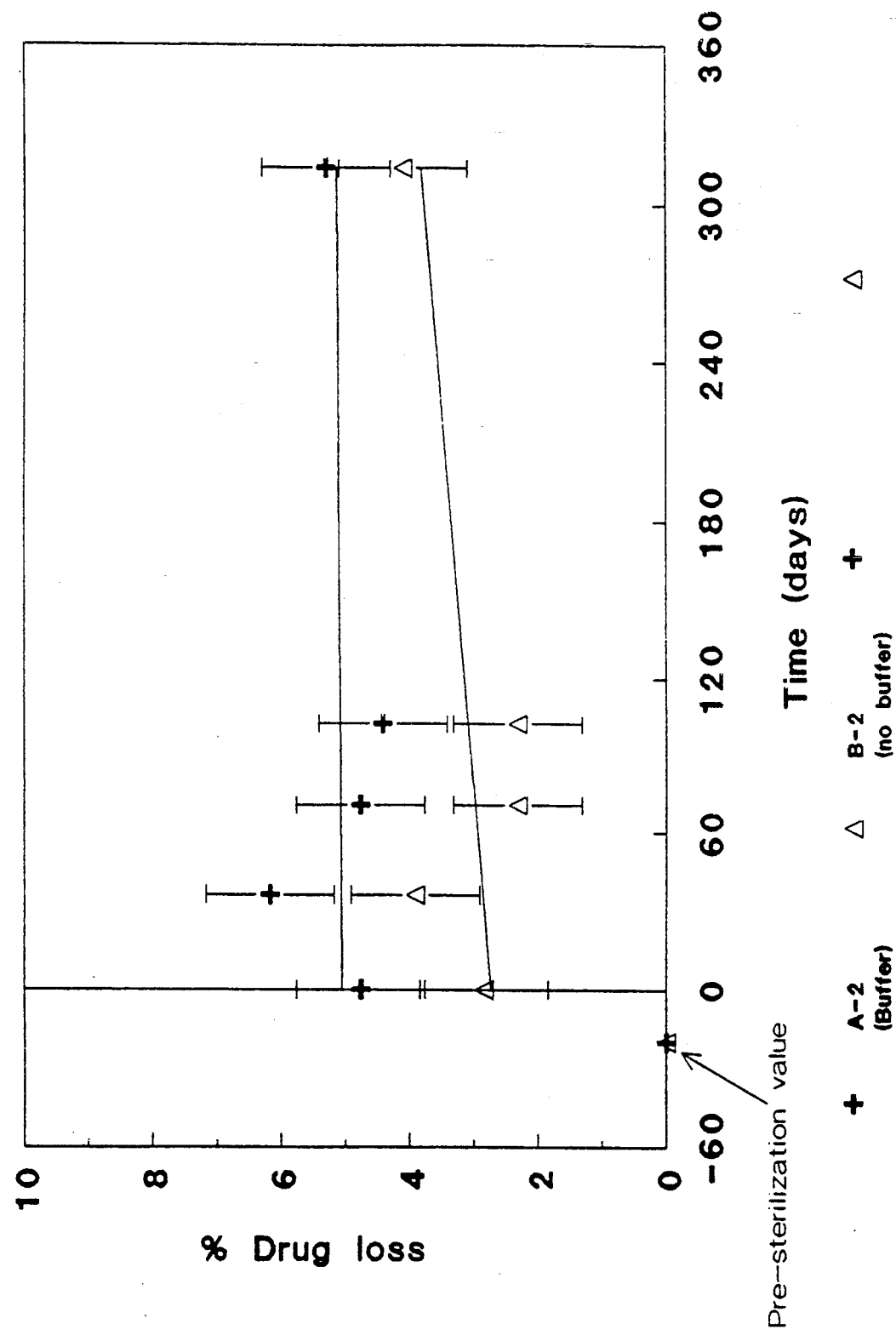
FIG. 2 illustrates graphically a further study of drug degradation over time for a buffered ranitidine solution versus a ranitidine formulation prepared pursuant to the present invention.

FIG. 2 illustrates graphically the results of the experiment stored at 25° C.

As in Example 1, the loss over sterilization was less for the non-buffered solution than for the buffered solution even though the non-buffered solution was at a pH that was believed to be less stable than the pH for the buffered solution.

EXAMPLE 3

In this example, buffered and non-buffered ranitidine samples, having differing pHs were compared for percent loss of ranitidine after terminal sterilization (steam sterilization). The samples were as follows:

| Test Configurations: | A-3 | B-3 |
|---|---|---|
| Bag Material | Plasticized PVC | Plasticized PVC |
| Bag Size | 250 ml | 250 ml |
| Concentration (mg/ml) | 0.54 | 0.54 |
| Buffer | phos/cit | none |
| Diluent | 0.9% NaCl | 0.9% NaCl |
| pH (initial) | 5/5.5/6/6.5 | 5/5.6/6/6.5 |

Again, the products were terminally sterilized and stored. Ranitidine degradation was measured as in Example 1.

| Results: | | |
|---|---|---|
| pH after sterilization | 5/5.5/6/6.5 | 5.5/5.8/6/6.3 |
| % loss on sterilization | 4.5/3.1/3.8/4.7 | −.3/−.8/.2/−.8 |
| % loss over 61 days @ 25° | 6.6/1.4/0/−.7 | 0.8/1.0/0/0.1 |
| Total loss (ster + 61 days) | 11/4.2/3.2/3.1 | 0.8/0/−1/0.1 |

Comments

A-4 and B-4 were the same formulations as A-3 and B-3 but they were filled into PVC containers that were constructed from minimally plasticized PVC as compared to the containers used for A-3 and B-3 having a different plasticizer.

The changes in A-3 and B-3 over sterilization and after 61 days at 25° C. were essentially equivalent to those for A-4 and B-4. All units for this study were sterilized at the same time.

Figure 3:
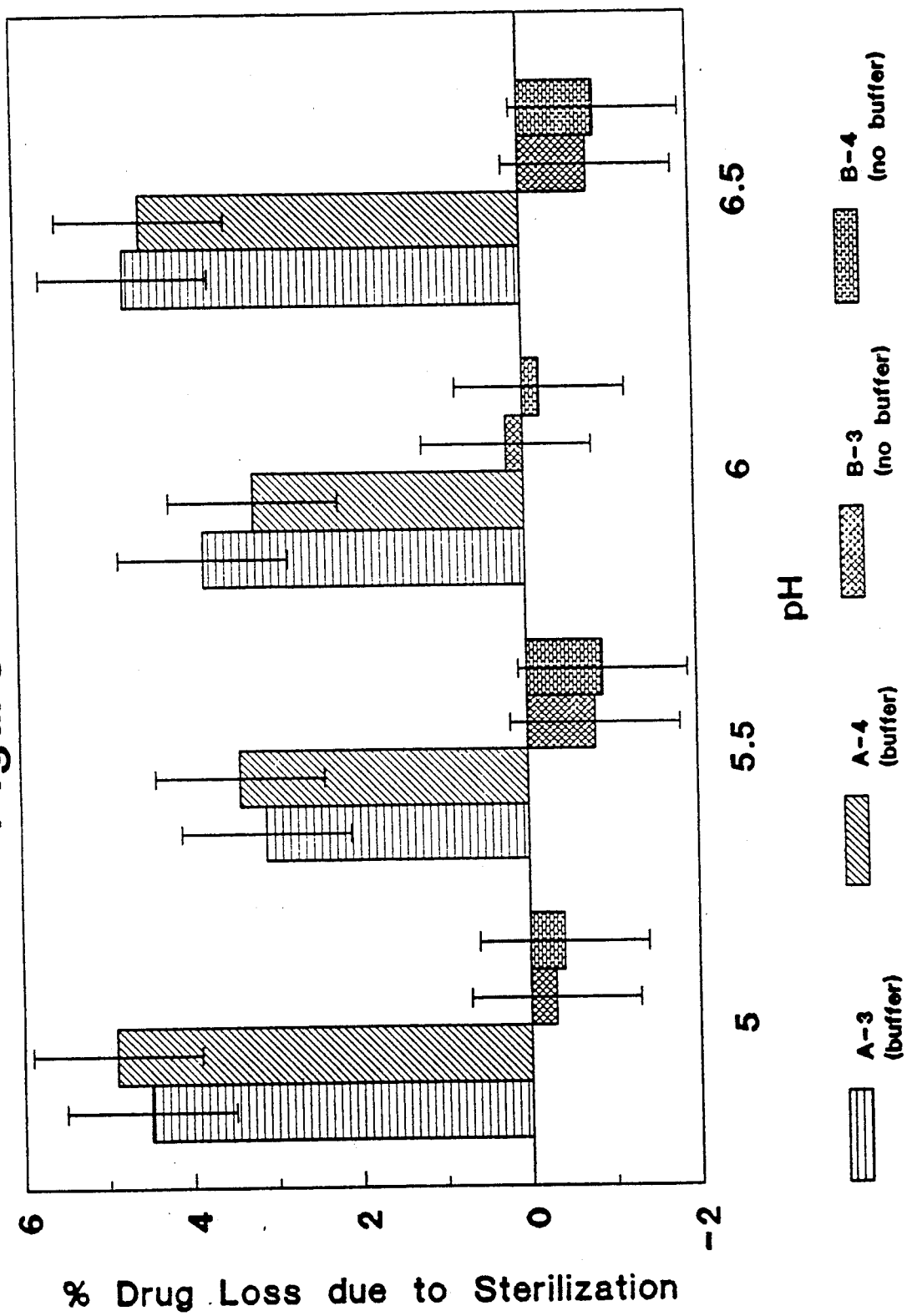
FIG. 3 illustrates graphically a comparison of drug loss over sterilization of buffered ranitidine formulations versus ranitidine formulations prepared pursuant to the present invention.

FIG. 3 illustrates graphically the test results.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A sterile pharmaceutical composition comprising: a sterile premixed unbuffered aqueous formulation containing an effective amount of ranitidine for the treatment of conditions mediated through histamine $H_2$ receptors, said formulation not having added, prior to administration or dispensing, any added buffer and the composition being sterile filled into a container.

2. A sterile pharmaceutical composition comprising: a sterile unbuffered premixed aqueous formulation containing an effective amount of ranitidine for the treatment of conditions mediated through histamine $H_2$ receptors, the formulation having a pH in the range of less than 6.5 to about 5.0, said formulation not having added prior to administration or dispensing any added buffer and the formulation being sterile filled into a container.

3. A process for making a premixed unbuffered pharmaceutical composition including ranitidine comprising the steps of:
adding a diluent, that does not include a buffer, to ranitidine and maintaining the pH of the resultant formulation at a pH of between less than 6.5 and greater than or equal to 5.0;
sterilizing the formulation by passing it through a filter into a container; and
sealing the container.

4. A process for making a premixed unbuffered pharmaceutical composition including ranitidine comprising the steps of:
adding a diluent, that does not include a buffer, to ranitidine and maintaining the pH of the resultant formulation at a pH of between less than 6.5 and greater than or equal to 5.0;
placing the formulation in a container; and
sterilizing the formulation by steam sterilization.

* * * * *